(12) United States Patent
Nozaki

(10) Patent No.: US 8,703,074 B2
(45) Date of Patent: Apr. 22, 2014

(54) CONTAINER ASSEMBLY AND METHOD FOR CONTAINING BIOLOGICAL GRAFT

(75) Inventor: Yusuke Nozaki, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 8 days.

(21) Appl. No.: 13/315,858

(22) Filed: Dec. 9, 2011

(65) Prior Publication Data

US 2012/0160714 A1  Jun. 28, 2012

(30) Foreign Application Priority Data

Dec. 22, 2010  (JP) ................................. 2010-286258

(51) Int. Cl.
*B01L 3/00*  (2006.01)

(52) U.S. Cl.
USPC .......................................... 422/559; 422/547

(58) Field of Classification Search
USPC ..................... 422/58, 99, 547, 549, 550, 559; 220/23.83, 23.87, 23.89, 23.9
See application file for complete search history.

(56) References Cited

U.S. PATENT DOCUMENTS

| | | | |
|---|---|---|---|
| 2,302,698 A * | 11/1942 | Kessel | ........................... 422/552 |
| 4,308,351 A | 12/1981 | Leighton et al. | |
| 4,897,358 A | 1/1990 | Carrasco | |
| 5,943,821 A | 8/1999 | Ducos et al. | |
| 6,939,516 B2 * | 9/2005 | Hall et al. | ...................... 422/553 |
| 2003/0086830 A1 | 5/2003 | Haywood et al. | |
| 2007/0175897 A1 | 8/2007 | Ellson | |
| 2007/0287159 A1 | 12/2007 | Chen | |

FOREIGN PATENT DOCUMENTS

| | | |
|---|---|---|
| DE | 1 017 751 B | 10/1957 |
| EP | 0 536 022 A1 | 4/1993 |
| EP | 0 816 488 A1 | 1/1998 |
| JP | 2002-335950 A | 11/2002 |
| JP | 2005-506526 A | 3/2005 |
| WO | 03/031064 A1 | 4/2003 |
| WO | 2009/136907 A1 | 11/2009 |

OTHER PUBLICATIONS

European Search Report for EP11 19 4874 dated Mar. 22, 2012.
Communication Pursuant to Article 94(3) EPC from European Patent App. No. 11194874.1 mailed on Jun. 18, 2013.

* cited by examiner

*Primary Examiner* — Jill Warden
*Assistant Examiner* — Dwayne K Handy
(74) *Attorney, Agent, or Firm* — Kenealy Vaidya LLP

(57) ABSTRACT

A container assembly for containing a biological graft can include a housing member sized to be able to contain the biological graft while keeping the size of an original shape of the biological graft. An aqueous fluid can fill the housing member such that the biological graft is contained in a suspended state in the aqueous fluid.

14 Claims, 10 Drawing Sheets

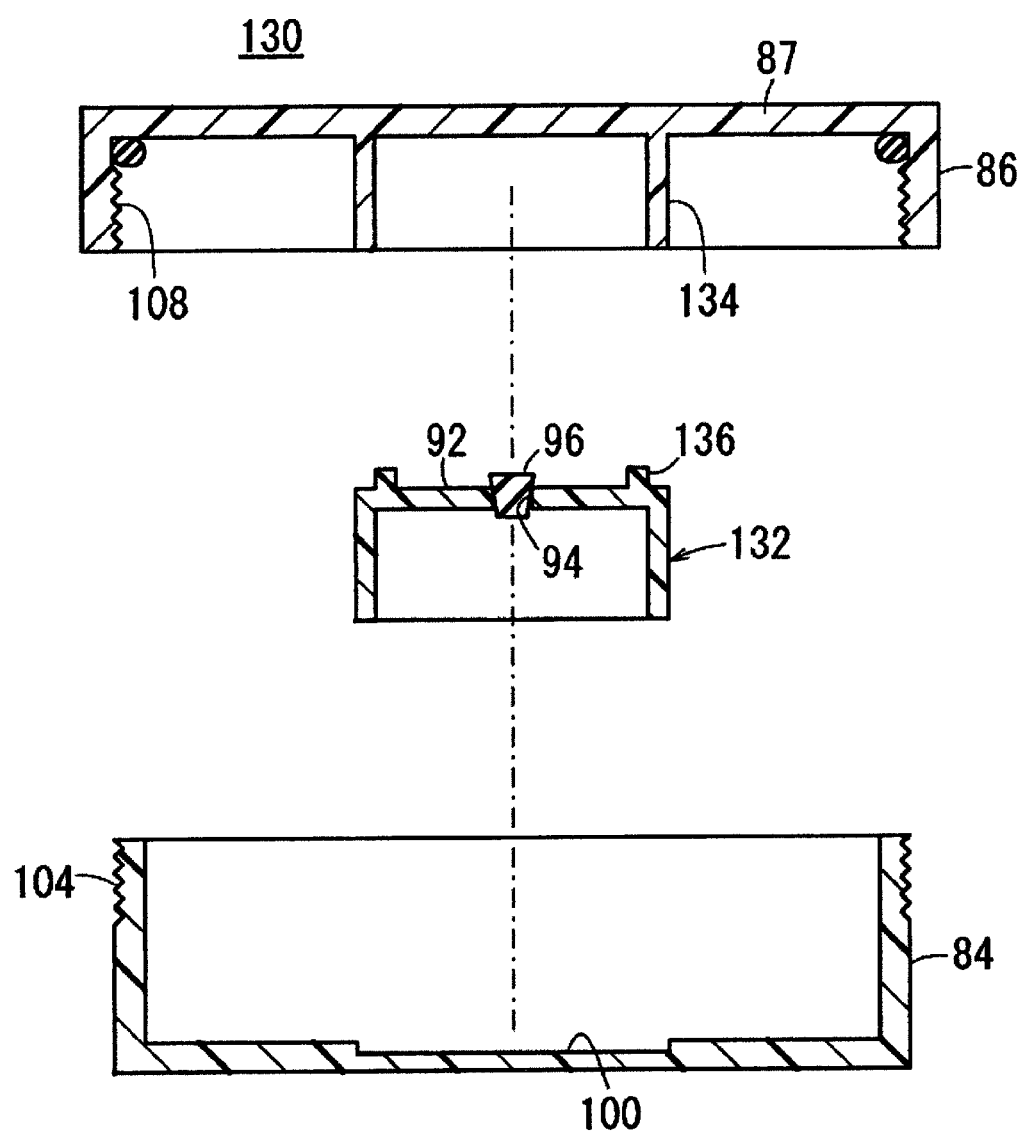

CONTAINER ASSEMBLY AND METHOD FOR CONTAINING BIOLOGICAL GRAFT

CROSS-REFERENCE TO RELATED APPLICATION

This application claims the priority benefit under 35 U.S.C. §119 of Japanese Patent Application No. JP2010-286258 filed on Dec. 22, 2010, which is hereby incorporated in its entirety by reference.

BACKGROUND

The presently disclosed subject matter relates to a container assembly and a containing method for a biological graft. The container assembly is configured to be used for storage and/or transportation of a biological graft having cells that are derived from a biological body.

In recent years, in connection with therapy of different organ and tissue diseases, and in particular with respect to myocardial infarction or the like, there has been widely known a therapeutic method in which a sheet-shaped cell culture product is obtained by cultivating a patient's own cells to form a tissue for transplant back to the patient (i.e., an autograft procedure). In general, this kind of cell culture product is sometimes called a "cell sheet." For the cultivated cell sheet to be preserved for transplantation to a patient, it is beneficial for the cell sheet to be contained in a predetermined container filled with a storage solution such as a physiological saline, and to be stored in this state and to be transported to a medical institution or the like in this state. Of course, such methods and apparatus can also be used for allograft type procedures.

In view of this, it may be contemplated to utilize a container assembly as described in Japanese Patent No. 4213588, for transportation of such a cell sheet. The container assembly includes a container capable of containing a reagent, and a sample holder which is disposed in the container and is capable of containing a biological sample therein. The sample holder is provided with a fluid opening section, through which the sample can be moved between the inside and the outside of the sample holder.

However, the cell sheet is fragile because of its very small thickness. In the case of using a container assembly, therefore, vibrations during transportation may be transmitted to the cell sheet through the storage solution resulting in collapse or breakage of the cell sheet, since the cell sheet is suspended only in the storage solution. Specifically, when the storage solution is shaken by vibrations applied to the container, liquid flow, such as waves, of the storage solution is generated, and shearing forces and/or tensile forces are exerted on the cell sheet. Therefore, there has been a long standing need for determining a way of preventing vibrations from being transmitted to the cell sheet.

In addition, Japanese Patent Laid-open No. 2002-335950 discloses a storage/transportation container having a configuration in which a membrane-shaped tissue is held by clamping the tissue with a liquid-permeable support from both sides thereof. The assembly is contained in a container together with a predetermined storage solution, while being kept in a wet state. In the case where the storage/transportation container is used for storage and/or transportation of a cell sheet, however, the cell sheet may be broken at the time of holding the cell sheet with the support, since the cell sheet is clamped from both sides thereof by the support which makes direct contact with the cell sheet.

SUMMARY

The presently disclosed subject matter has been made in consideration of the above-mentioned characteristics, features, problems, and attributes of the conventional art and practices of medical technology. According to an aspect of the presently disclosed subject matter, a container assembly and a containing method for a biological graft can be provided by which a biological graft having cells that are derived from a biological body can be contained, without spoiling the original shape of the graft, and while keeping the quality and biological activity of the graft, and which can be stored and transported easily.

According to another aspect of the presently disclosed subject matter, there is provided a container assembly for containing a biological graft having cells that are derived from a biological body, to be used for storage and/or transportation of the membrane-shed tissue, including: a housing member sized to be able to contain the biological graft while keeping the size of an original shape of the biological graft; and an aqueous fluid (storage solution) filling the housing member, wherein the biological graft is contained in a suspended state in the aqueous fluid.

According to the configuration as described above, the housing member can be filled with the aqueous fluid with little or no air contained, and the biological graft can be suspended in the aqueous fluid. This ensures that, even when vibrations are generated during transportation of the container assembly and the housing member is vibrated, waves or flow of the aqueous fluid inside the housing member can be prevented. As a result, vibrations can be prevented from being directly transferred to the biological graft, and the biological graft can be prevented from being broken.

In the container assembly for the biological graft as described above, the container assembly can further include an outer housing member for containing the housing member; in addition, the housing member can have a lower-side opening section which is open to the lower side and is greater in plan-view shape than the biological graft, and the lower-side opening can be closed by contact of a lower end of the housing member with the surface of a bottom section of the outer housing member.

According to the above configuration, at the time of taking out the biological graft, it is unnecessary to transfer the biological graft and the aqueous fluid into another container. Therefore, the taking-out operation can be carried out quickly, and the risk of breakage of the biological graft attendant on a transferring operation can be essentially obviated.

In the container assembly for the biological graft as described above, a fluid (liquid) which is the same as or different from the aqueous fluid (storage solution) can be contained in the outer housing member on the outside of the housing member.

With the fluid thus present in the surroundings of the housing member, air can be prevented from flowing into the housing member through the lower-side opening section.

The container assembly for the biological graft as described above can further include a stabilizing member floating on the surface of the fluid present outside the housing member in the inside of the outer housing member.

With such a stabilizing member disposed, the housing member and the fluid can be stabilized. Consequently, even when severe vibrations are exerted, the lower end of the housing member can be prevented from being exposed to air, and in-flow of air into the housing member can be prevented.

In the container assembly for the biological graft as described above, a gel-like material may be contained in the outer housing member on the outside of the housing member. With the gel-like material thus present in the surroundings of the housing member, air can be prevented from flowing into the housing member through the lower-side opening section. In addition, with the housing member held by the gel-like material, the housing member is prevented from moving.

In the container assembly for the biological graft as described above, the outer housing member can have an outer housing member body (container body) having an upper-side opening section opening to the upper side and a covering member capable of closing the upper-side opening section. The container assembly can further include a connecting mechanism for connecting the outer housing member body and the covering member to each other. An intervening member which is clamped between the housing member and the covering member when the outer housing member body is closed with the covering member can be provided at an upper portion of the housing member.

According to this configuration, the housing member is pressed by the outer housing member body, whereby the housing member is stably fixed. This ensures that the housing member is prevented from being horizontally and/or vertically shifted inside the outer housing member body. In addition, the lower end of the housing member can be prevented from floating up from the surface of the bottom section of the outer housing member body. Consequently, the state in which the housing member is filled up with the aqueous fluid can be suitably maintained.

In the container assembly for the biological graft as described above, an upper end of the intervening member can form a line or surface contact with the covering member when the outer housing member body is closed with the covering member. This enables the housing member to be stably held, without need to provide another member for stabilizing the position of the housing member, at an outer peripheral surface of the housing member.

In the container assembly for the biological grafts as described above, the connecting mechanism can include at least one clip which makes contact with a lower surface of the outer housing member body and an upper surface of the covering member to thereby elastically constrain the outer housing member body and the covering member.

This ensures that even where the outer housing member is formed from a comparatively easily pliable material, it is possible, by constraint (pressing) from the upper surface and the lower surface of the outer housing member by the clips, to securely press the housing member against the outer housing member body by the covering member and thereby to fix the housing member more stably.

In the container assembly for the biological graft as described above, a wall of the housing member may be formed with a hole in communication with the inside and the outside of the housing member, and the hole may be closed with an occluding member. According to this configuration, air inside the housing member can be discharged through the hole, so that the inside of the housing member can be easily filled up with an aqueous fluid.

In the container assembly for the biological graft as described above, a horizontal positioning-determining member for horizontal positioning of the housing member relative to the outer housing member body can be provided at a bottom section of the outer housing member body. This ensures that the housing member is prevented from being horizontally shifted in relation to the outer housing member body, and the biological graft can be held in a stable manner.

In addition, according to another embodiment of the presently disclosed subject matter, there can be provided a method of containing a biological graft having cells that are derived from a biological body, including: preparing a housing member sized to be able to contain the biological graft while keeping the size of an original shape of the biological graft; and containing the biological graft in a suspended state in an aqueous fluid (storage solution) contained in the housing member to the extent that that air is not contained in the housing member.

The method of containing the biological graft as described above can include: suspending the biological graft in the aqueous fluid contained in an outer housing member body of an outer housing member; positioning the housing member having a lower-side opening section opening to the lower side so that a lower end of the housing member is located in the aqueous fluid and kept away from the surface of a bottom section of the member body; discharging air present in the housing member by use of a tubular member through a gap between the lower end of the housing member and the surface of the outer housing member body so as to fill up the housing member with the aqueous fluid; placing the housing member on the surface of the bottom section of the outer housing member body to thereby suspend the biological graft in the aqueous fluid in the housing member; and closing the outer housing member body with a covering member so that the housing member containing the biological graft is hermetically sealed in the outer housing member.

The method of containing the biological graft as described above can include: suspending the biological graft in the aqueous fluid contained in an outer housing member body of an outer housing member; placing the housing member, which has a lower-side opening section opening to the lower side and a hole formed in a wall thereof, on the surface of a bottom section of the outer housing member body so as to fill up the housing member with the aqueous fluid and to suspend the biological graft in the aqueous fluid in the housing member; and closing the outer housing member body with a covering member so that the housing member containing the biological graft is hermetically sealed in the outer housing member.

According to the container assembly and the containing method for a biological graft pertaining to embodiments of the presently disclosed subject matter, the biological graft can be contained, without spoiling the original shape thereof, and while keeping the quality and biological activity thereof, and such that the graft can be easily stored and/or transported.

According to another aspect of the disclosed subject matter, a container assembly configured to contain a biological graft can include a housing member having a top end, a lower end, and a wall located at the lower end defining a lower end opening in the housing member. The container assembly can include a container body having a lower surface configured to mate with the wall of the lower end opening of the housing member to define a chamber within the housing member, the chamber being configured to contain aqueous fluid and the biological graft suspended in the aqueous fluid. A covering member can be configured to connect to the container body and contact with the housing member to maintain contact between the wall of the lower end opening of the housing member and the lower surface of the container body in order to form the chamber. A connecting structure can be configured to connect the covering member and the container body and to maintain contact between the wall of the lower end opening of the housing member and the lower surface of the container body in order to form the chamber.

According to another aspect of the disclosed subject matter, the connecting structure can be configured as one of, a clip, and a screw and thread structure located on the container body and the covering member.

According to another aspect of the disclosed subject matter, the container assembly can include a housing member with an aperture in the top end and an occluding member configured to seal the aperture in the housing member such that the chamber is hermetically sealed when the occluding member is located in the aperture and the container body is connected with the covering member by the connecting structure.

According to yet another aspect of the disclosed subject matter, the container assembly can include a fluid located in the container body outside of the housing member. In one exemplary embodiment, the fluid can be formed as a gel.

According to another aspect of the disclosed subject matter, the container assembly can include a stabilizing member located in the container body and configured to stabilize a fluid located within the container body in order to prevent wave formation in the fluid.

According to still another aspect of the disclosed subject matter, the housing member of the container assembly can include an intervening member located at the top end of the housing member and configured to contact the covering member and be clamped between the covering member and the container body when the container body is closed with the covering member.

According to another aspect of the disclosed subject matter, the intervening member can be formed integrally with the lower end of the housing member and as a one piece continuous material with the housing member.

According to yet another aspect of the disclosed subject matter, the intervening member can be formed integrally with the covering member and as a one piece continuous material with the covering member.

According to still another aspect of the disclosed subject matter, the intervening member can be an elastic member located between the covering member and the lower end of the housing member.

According to another aspect of the disclosed subject matter, the intervening member can be a rigid structure having a wall and an aperture located in the wall and an occluding member located in the aperture, and the housing member can include a separate rigid tubular structure.

According to still another aspect of the disclosed subject matter, the container body of the container assembly can include a horizontal positioning-determining structure configured to horizontally position the housing member relative to the container body, wherein the horizontal positioning-determining member extends upward from the lower surface of the container body and is located immediately adjacent an outer peripheral wall of the housing member.

BRIEF DESCRIPTION OF THE DRAWINGS

These and other characteristics and features of the presently disclosed subject matter will become clear from the following description with reference to the accompanying drawings, wherein:

FIG. 9 is an exploded perspective view of a container assembly for containing a biological graft according to another modification of the embodiment of FIG. 5.

DETAILED DESCRIPTION OF EXEMPLARY EMBODIMENTS

Now, exemplary embodiments of a container assembly and method for containing a biological graft, to be used for storage and/or transportation of a biological graft having cells that are derived from a biological body, according to the presently disclosed subject matter will be described with reference to the exemplary embodiments and referring to the attached drawings.

Figure 1:
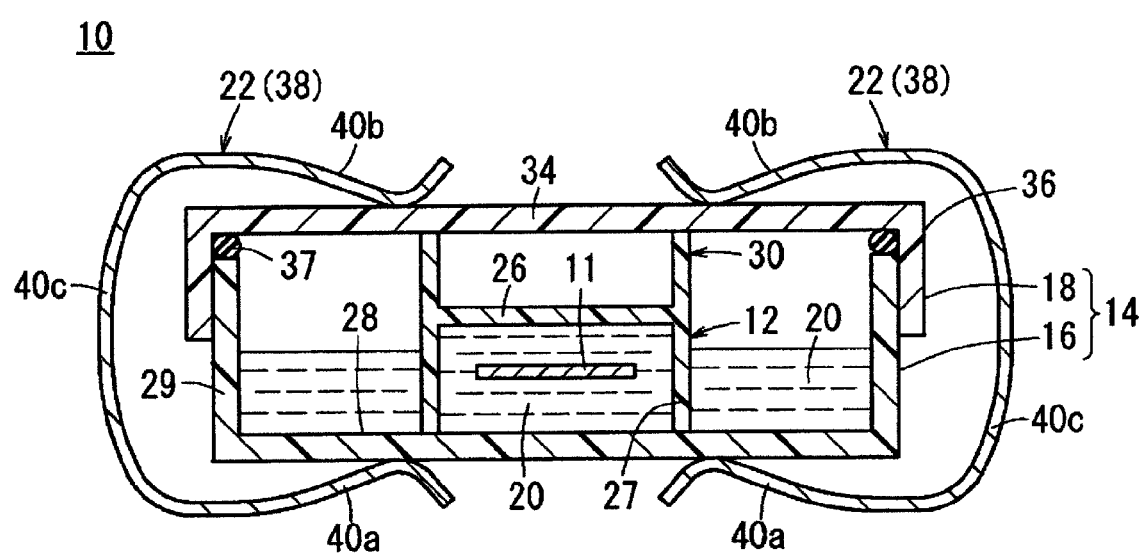
FIG. 1 is a sectional view of a container assembly for containing a biological graft according to an embodiment of the presently disclosed subject matter.
Figure 2:
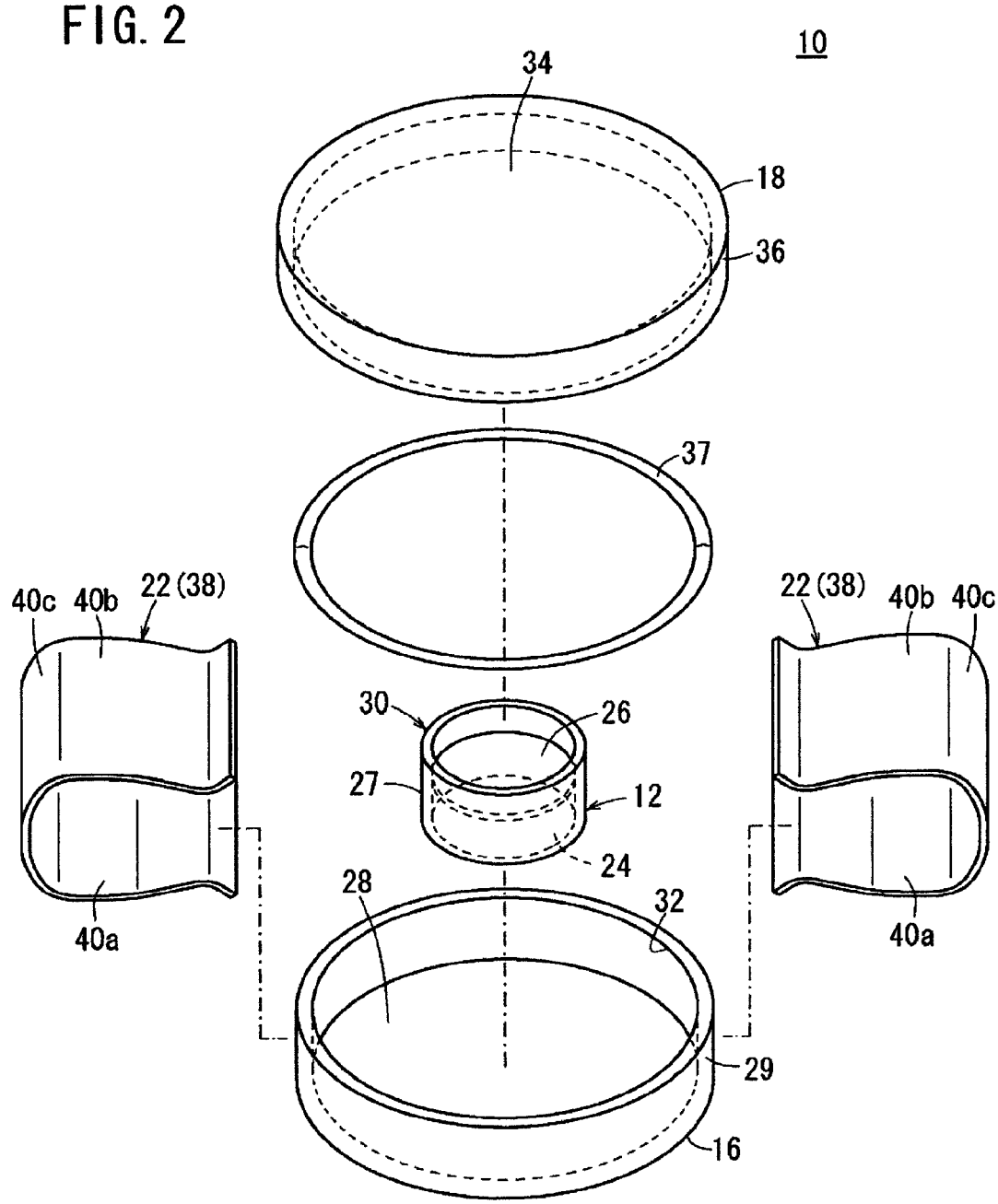
FIG. 2 is an exploded perspective view of the container assembly shown in FIG. 1.

FIG. 1 is a sectional view of a container assembly 10 for containing a biological graft (hereafter referred to simply as "container 10") according to a first exemplary embodiment, and FIG. 2 is an exploded perspective view of the container 10. The container 10 is a device to be used for storage and/or transportation of a biological graft 11 having cells that are derived from a biological body. The container 10 includes a housing member 12 for containing the biological graft 11, an outer housing member 14 which includes a container body (outer housing member body) 16 and a covering member 18 and which contains the housing member 12. A storage solution (aqueous fluid) 20 can be contained in the housing member 12 and the outer housing member 14. The container 10 can also include a connecting mechanism 22 for connecting the container body 16 of the outer housing member 14 and the covering member 18 to each other.

The biological graft 11 to be stored and/or transported can be a structure which is derived from a biological body. The biological graft has a certain extent of thickness and can be used for treatment of mammals, for example, humans. Treatment includes regeneration, therapy, or promotion of healing with respect to disease, sickness, injury or deficiency of a part or the whole part of an organ or tissue. The organ or tissue includes heart, muscle, cornea, retina, blood vessel, nerve, epidermis, dermis, cartilage, tooth, etc. or any/all of a plurality of organs. The biological graft can also be used for examination of irritant property, sensitization property or toxicity of chemicals to organs or tissues, effects of drugs on the organs or tissues, reactions of drugs on tissues, or the like. Thus, examples of the biological graft 11 include a membrane-shaped tissue, dermal tissue, mucoepithelial tissue, ectocornea tissue, cultivated skin, cultivated dermis, cultivated epidermis, cultivated epitherlial tissue, cultivated corneal tissue, cartilaginous tissue, retinal tissue, neurofilament, artificial blood vessel, myoblastic tissue, sheet-shaped cell culture product formed from the above-mentioned cells that are derived from a biological body, etc.

A sheet-shaped cell culture product can be used which is formed from myoblasts. The sheet-shaped cell culture product may also contain fibroblasts. The sheet-shaped cell culture product 11 may be composed only of cells or extracellular matrix secreted by cells. The sheet-shaped cell culture product 11 may also include a substance not derived from a biological body, such as a support or scaffold.

The housing member 12 is container sized to be able to contain the biological graft 11 while keeping the size of an original shape of the biological graft 11 (keeping the original size and shape of the biological graft 11, as it is), and functions as an inner container (inner housing member) by being contained in the outer housing member 14. The housing member 12 can be a tubular body having a lower-side opening section 24 (see FIG. 2) opening to the lower side, and can be formed as a hollow cylindrical body in the example shown. The housing member 12 in the example shown has an upper wall 26, and a tubular wall section 27 extending downward from an outer peripheral edge portion of the upper wall 26. When the housing member 12 is placed on the surface of a bottom section 28 of the outer housing member 14, the lower-side opening section 24 is closed, whereby a closed space is formed inside the housing member 12.

The storage solution (aqueous fluid) 20 for storage of the biological graft 11 can be contained in the housing member 12 to the extent that air is not contained in the housing member 12. In other words, the inside of the housing member 12 can be substantially entirely filled up with the storage solution 20 so that no air layer or big air bubble is formed or left, for example on the upper side therein. The expression "the storage solution 20 is contained in the housing member 12 to the extent that air is not contained in the housing member 12" means that the presence of some small bubbles in an upper portion of the inside of the housing member 12 is allowed. Even when some small bubbles are present in an upper portion of the inside of the housing member 12, there is little possibility of generation of waves or flow of the storage solution 20 inside the housing member 12 when the housing member 12 is vibrated. Examples of the storage solution 20 include liquid medium, physiological saline, isotonic solution, buffer, and Hanks' balanced salt solution.

At an upper portion of the housing member 12, an intervening member 30 can be clamped between a portion of the housing member 12 and the covering member 18 when the container body 16 is closed with the covering member 18. While the intervening member 30 in the example shown has a hollow cylindrical shape, it may have a tubular shape with a non-circular section, or may be projecting pieces formed, or as if formed, by splitting a tubular shape with a circular or non-circular section into a plurality of pieces arrayed along the circumferential direction. Alternatively, a configuration may be adopted in which an upper portion of the intervening member 30 is closed with a wall and the wall is put into surface contact with the lower surface of the covering member 18. In addition, the intervening member 30 can be considered to be a portion of the housing member 12, whether integral therewith or separate therefrom.

The intervening member 30 in the example shown is formed integrally with the upper portion of the housing member 12. The outside diameter of the intervening member 30 may not necessarily be equal to the outside diameter of the housing member 12 as in the example shown; namely, it may be smaller than or greater than the outside diameter of the housing member 12. In addition, the intervening member 30 need not be integrally formed and can be a separate member.

The outer housing member 14 can include the container body 16 and the covering member 18, and can be greater in size than the housing member 12. Specifically, the outer housing member 14 can have such a size that a space (for example, an annular space) is formed between the outer periphery of the housing member 12 and the inner periphery of the outer housing member 14 in a state in which the housing member 12 is contained in the outer housing member 14. In addition, the outer housing member 14 can be so sized that a sufficient working space can be secured at the time of detaching the housing member 12 from the outer housing member 14 and taking out the biological graft 11 suspended in the storage solution 20 by use of an appropriate instrument (transplanting device or the like). For instance, where the outer housing member 14 is a circular laboratory dish, its inside diameter can be about 30 to 300 mm, and possibly about 80 to 150 mm.

The container body 16 can be a small-height bottomed tubular body (a bottomed hollow cylindrical body, in the example shown) having a bottom section 28 and a side wall section 29 extending upward from an outer peripheral edge portion of the bottom section 28. An upper portion of the container body 16 can be formed as an upper-side opening section (see FIG. 2) which is open on the upper side. The covering member 18 can be formed so as to be capable of closing the upper-side opening section 32 of the container body 16, and can have a top section 34 and a side wall section 36 extending downward from an outer peripheral edge portion of the top section 34. The inside diameter of the side wall section 36 can be substantially equal to or slightly greater than the outside diameter of the side wall section 29 of the container body 16. An annular seal member 37 can be provided on the lower surface of an outer peripheral portion of the top section 34. When the container body 16 is closed with the covering member 18, the gap between the covering member 18 and the container body 16 can be sealed by the seal member 37, whereby the outer housing member 14 is hermetically sealed liquid-tight. Incidentally, the same sealing effect as described above can also be obtained by providing the seal member 37 on the upper surface of the side wall section 29 of the container body 16, instead of providing the seal member 37 on the lower surface of the top section 34 of the covering member 18. The seal member 37 is a member for preventing leakage of liquid, and is formed, for example, from silicone or butadiene rubber.

The materials constituting the housing member 12, the container body 16 and the covering member 18 are not specifically restricted. Examples of the materials which can be used here include various resins such as, for example, polyvinyl chloride, polyethylene, polypropylene, cyclic polyolefin, polystyrene, poly(4-methylpentene-1), polycarbonate, acrylic resin, acrylonitrile-butadiene-styrene copolymer, polyesters such as polyethylene terephthalate, polyethylene naphthalate, etc., butadiene-styrene copolymer, polyamides (e.g., 6-nylon, 6,6-nylon, 6,10-nylon, 12-nylon), glasses, ceramics, metals, and alloys. In addition, the materials constituting the housing member 12, the container body 16 and the covering member 18 can be substantially transparent, for securing visibility of the inside of the container assembly 10. Further, these materials can have surfaces which are non-adhesive to cells, for preventing adhesion of cells thereto.

In a state in which the covering member 18 and the container body 16 are connected to each other by the connecting mechanism 22 and in which the container body 16 is closed by the covering member 18, the housing member 12 can be clamped between the container body 16 and the covering member 18, and thereby restrained from moving with respect to the outer housing member 14. As a result, the housing member 12 can be stably fixed inside the outer housing member 14.

The storage solution 20 can be contained in the space which is inside the outer housing member 14 and is outside the housing member 12. The liquid level of the storage solution 20 outside the housing member 12 can be below the liquid level of the storage solution 20 inside the housing member 12. This ensures that the atmospheric pressure produces a force for pressing the housing member 12 to the surface of the bottom section 28 of the container body 16, so that the housing member 12 can be stably fixed by the container body 16. In addition, a liquid different from the storage solution 20 can be contained, in place of the storage solution 20, on the outside of the housing member 12.

The connecting mechanism 22 in the example shown includes two clips 38 which make contact with both the lower surface of the container body 16 and the upper surface of the covering member 18, respectively, so as to elastically constrain the container body 16 and the covering member 18. Each of the clips 38 includes a pair of arm sections 40a and 40b extending while facing each other, and a connecting section 40c interconnecting base end portions of the pair of arm sections 40a, 40b. Each of the clips 38 can be opened wide through elastic deformation of the pair of arm sections 40a and 40b toward the outer sides. The spacing between the pair of arm sections 40a and 40b in a natural state of the clip 38 (in a state in which no external force is applied to the clip 38) is smaller than the thickness (height) of the outer housing member 14 in the state in which the container body 16 is closed with the covering member 18. Such a clip 38 can be formed from any of elastic metals, alloys, resins and the like.

In FIG. 1, the two clips 38 are mounted to the outer housing member 14 at positions on opposite sides. This, however, is not limitative. The number of the clips 38 to be thus mounted may be set in a range such that the covering member 18 and the container body 16 can be connected to each other with an appropriate holding force by the clips 38. Thus, the number of the clips 38 may be one or may be two, three or more.

The container 10 according to the present embodiment, basically, is configured as-described above. Now, exemplary modes of operation and effects of the container 10 will be described below.

Figure 3A:
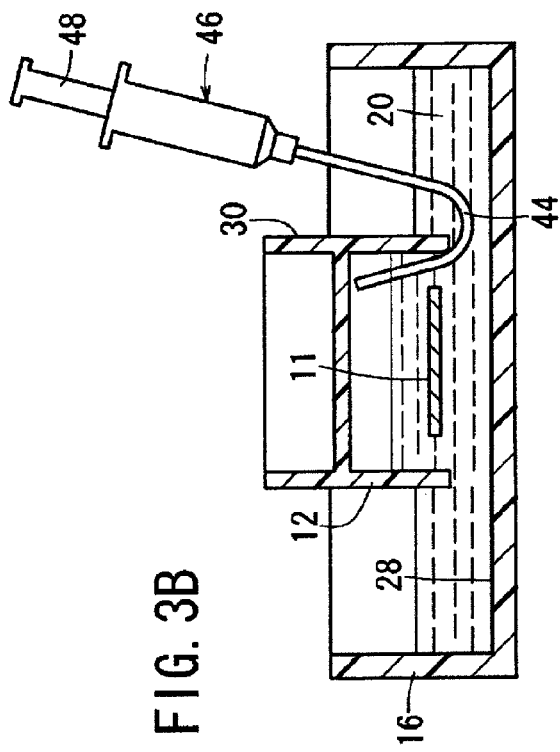
FIG. 3A is a view of a first state illustrating a method of assembling the container assembly shown in FIG. 1.
Figure 3B:
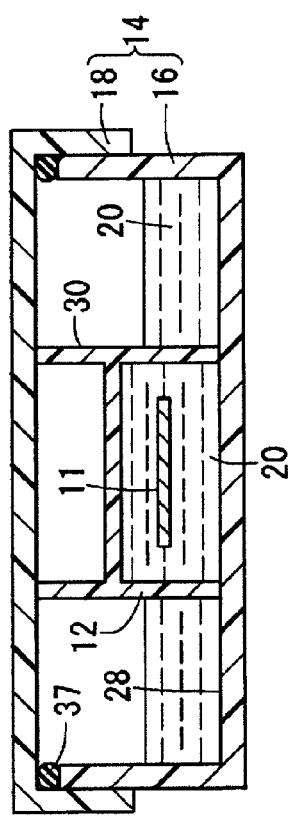
FIG. 3B is a view of a second state illustrating the method of assembling the container assembly shown in FIG. 1.

In order to assemble the container 10 as described above, first, as shown in FIG. 3A, the storage solution 20 is placed in the container body 16, and the biological graft 11 is suspended in the storage solution 20. Next, as shown in FIG. 3B, the biological graft 11 and the surrounding storage solution 20 are covered by the housing member 12, and the housing member 12 is so disposed that the whole circumference of the lower end of the housing member 12 is located in the storage solution 20 and that the whole circumference of the lower end of the housing member 12 is spaced from the surface of the bottom section 28 of the container body 16. Thereafter, in this state, the air present inside the housing member 12 is discharged by use of, for example, a suction mechanism (a syringe 46, in the example shown) having a curved nozzle (tubular member) 44.

Specifically, the curved nozzle 44 is inserted into the housing member 12 through the gap between the lower end of the housing member 12 and the surface of the bottom section 28 of the container body 16 and, in this state, a plunger 48 of the syringe 46 is pulled, whereby the air present inside the housing member 12 is sucked away. In this case, at the final stage of the suction, bubbles are left inside the housing member 12. However, the bubbles can be substantially and/or completely removed from the inside of the housing member 12 by a method in which the housing member 12 is inclined to move the bubbles to a corner zone. A tip portion of the nozzle 44 is then positioned in the corner zone and suction is carried out. Where the housing member 12 is composed of a transparent member, the above-mentioned operation can be carried out while visually checking the presence and position of the bubbles, so that removal of the bubbles can be performed speedily and assuredly.

Figure 3C:
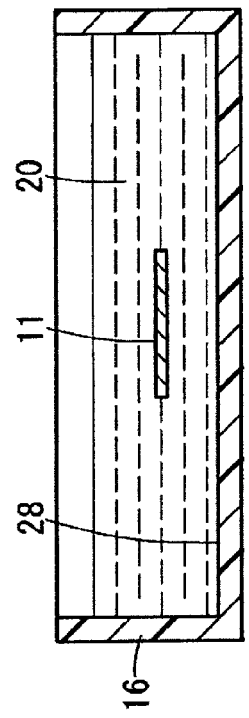
FIG. 3C is a view of a third state illustrating the method of assembling the container assembly shown in FIG. 1.

After the air is removed from the inside of the housing member 12 and the housing member 12 is filled up with the storage solution 20, the housing member 12 is placed on the surface of the bottom section 28 of the container body 16, as shown in FIG. 3C. In this instance, if the liquid level of the storage solution 20 outside the housing member 12 is above the liquid level of the storage solution 20 inside the housing member 12, the amount of the storage solution 20 outside the housing member 12 is reduced so that the liquid level of the storage solution 20 outside the housing member 12 will be below the liquid level of the storage solution 20 inside the housing member 12.

Figure 3D:
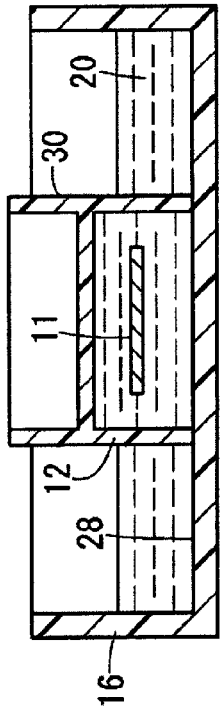
FIG. 3D is a view of a fourth state illustrating the method of assembling the container assembly shown in FIG. 1.

Then, the container body 16 is closed with the covering member 18 (see FIG. 3D), and the container body 16 and the covering member 18 are connected to each other by the above-mentioned clips 38. As a result, the housing member 12 is clamped between the covering member 18 and the container body 16 through the intervening member 30, so that the housing member 12 is stably fixed inside the outer housing member 14. By the above-mentioned process, the container 10 in the state shown in FIG. 1 is completed. Incidentally, the above-mentioned working steps for assembling the container 10 can be carried out in a clean room (in an aseptic environment).

According to the container 10 configured as above, the housing member 12 is filled up with the storage solution 20, and the biological graft 11 is suspended in the storage solution 20. This ensures that even if vibration is generated during transportation of the container 10 and the housing member 12 is vibrated, waves or flow of the storage solution 20 inside the housing member 12 are not generated. Therefore, transmission of vibration to the biological graft 11 is obviated, so that the biological graft 11 can be prevented from being broken.

In addition, in the present embodiment, the housing member 12 can be provided with the lower-side opening section 24, and the lower-side opening section 24 can be closed by the contact of the lower end of the housing member 12 with the surface of the bottom section 28 of the outer housing member 14. This ensures that, in the process of taking out the biological graft 11, the biological graft 11 contained in the housing member 12 is moved toward the container body 16 side by only lifting up the housing member 12 relative to the container body 16. Therefore, it is unnecessary to transfer the biological graft 11 and the storage solution 20 into another container, so that the operation can be carried out speedily. Besides, the possibility of breakage of the biological graft 11 during such a transferring operation can be essentially obviated.

In the present embodiment, the storage solution 20 can be contained outside the housing member 12, so that air can be prevented from flowing into the housing member 12 through the lower-side opening section 24 of the housing member 12. The lowest circumferential end of the lower-side opening section 24 forms a surface (an edge face) facing the bottom surface of the housing member 12, which contacts the bottom surface of the housing member 12 and creates a gap between the lower-side opening section 24 and the bottom surface of the housing member 12. Around this gap, the lateral surface of the lower-side opening section 24 (close to the surface facing the bottom surface of the housing member 12) is surrounded with and contacts the storage solution both inside and outside the lower-side opening section 24. To be more specific, in the case where the storage solution 20 is absent on the outside of the housing member 12, the storage solution 20 present inside the housing member 12 may leak out through the gap between the housing member 12 and the surface of the bottom section 28 of the container body 16, and air may flow into the housing member 12. Since the storage solution 20 is present in the surroundings of the housing member 12, however, such flowing-in of air is inhibited.

Incidentally, after the air present inside the housing member 12 is discharged and the housing member 12 is placed on the surface of the bottom section 28 of the container body 16, the storage solution 20 outside the housing member 12 may be removed and a gel-like material may be placed as substitute for the storage solution 20 thus removed. The presence of the gel-like material in the surroundings of the housing member 12 ensures that in-flow of air into the housing member 12 through the lower-side opening section 24 can be prevented from occurring. In addition, with the housing member 12 held by the gel-like material, the housing member 12 is inhibited from moving, so that the housing member 12 can be fixed more stably.

In the present embodiment, the intervening member 30 is provided at an upper portion of the housing member 12, and, when the container body 16 is closed with the covering member 18 and these are fixed by the clips 38, the covering member 18 presses the housing member 12 against the container body 16 through the intervening member 30, so that the housing member 12 is stably fixed inside the outer housing member 14. This prevents the housing member 12 from horizontally shifting inside the outer housing member 14. In addition, the lower end of the housing member 12 is prevented from floating up from the surface of the bottom section 28 of the container body 16. Consequently, the state in which the housing member 12 is filled up with the storage solution 20 can be suitably maintained.

Besides, in the present embodiment, in the state in which the container body 16 is closed with the covering member 18, the upper end of the intervening member 30 makes not point contact but line (circumference) contact with the covering member 18. This makes it possible to stably hold the housing member 12, without need to provide another member for stabilizing the housing member 12, at the outer circumferential surface of the housing member 12.

Furthermore, in the present embodiment, the connecting mechanism 22 can be composed of the clips 38. This ensures that even where the outer housing member 14 is formed from a comparatively easily pliable material such as resin material, it is possible, by constraint (pressing) from the upper surface and the lower surface of the outer housing member 14 by the clips 38, to securely press the housing member 12 against the container body 16 by the covering member 18 and thereby to fix the housing member 12 more stably. Incidentally, in the case where the connecting mechanism 22 is composed of the clips 38, the tip portions (the portions put into contact with the outer housing member 14) of the arm sections 40*a* and 40*b* of the clips 38 can constrain (press) the portions at which the housing member 12 and the intervening member 30 make contact with the outer housing member 14.

In order to take out the biological graft 11 from the container 10 set in the state shown in FIG. 1, first, the clips 38 are dismounted to release the covering member 18 and the container body 16 from the fixed state, and the covering member 18 is detached from the container body 16. Next, the housing member 12 is lifted up in relation to the container body 16, whereby the biological graft 11 inside the housing member 12 is transferred to the container body 16, together with the storage solution 20. Incidentally, before the housing member 12 is lifted up relative to the container body 16, an additional amount of the storage solution 20 may be supplied to the outside of the housing member 12 so as to raise the liquid surface of the storage solution 20 outside the housing member 12 above the liquid surface inside the housing member 12, whereby the housing member 12 can be lifted up more easily due to buoyancy.

In place of the above-mentioned transferring method, the following method may also be adopted. First, the housing member 12 is lifted up to such an extent that the lower end of the housing member 12 is not completely exposed from the storage solution 20 inside the container body 16. In this condition, the curved nozzle 44 of the syringe 46 shown in FIG. 3B is inserted into the housing member 12 through the gap between the lower end of the housing member 12 and the surface of the bottom section 28 of the container body 16. Then, air is fed into the housing member 12 through the nozzle 44, whereby the storage solution 20 is discharged from the housing member 12. When such a method is adopted, the housing member 12 can be dismounted from the container body 16 without causing considerable flow of the storage solution 20. Accordingly, the possibility of breakage of the biological graft 11 due to flow of the storage solution 20 can be eliminated.

In the container 10 as described above, air may be present on the upper side of the storage solution 20 which is present outside the housing member 12 in the inside of the outer housing member 14. Therefore, when vibration is applied to the container 10, the storage solution 20 in this zone may be put into motion, and generation of waves at the liquid surface thereof may occur. Depending on the intensity of the waves or the like, therefore, the lower end of the housing member 12 may momentarily be exposed to air. In view of this, a container 50 according to a modification shown in FIG. 4A may include a stabilizing member 52 disposed within the container 50 such that the stabilizing member 52 floats on the surface of the storage solution 20 present outside the housing member 12 in the inside of the outer housing member 14. Such a stabilizing member 52 can be composed of foamed polystyrene or film having an intermediate shape (an annular shape, in the present modification) between the shape of the housing member 12 and the shape of the outer housing member 14. The stabilizing member 52 may take the shape of the space (exclusive of the storage solution 20) between the housing member 12 and the outer housing member 14 (for example, a thick annular shape).

With such a stabilizing member 52 disposed, the housing member 12 and the storage solution 20 can be stabilized. Consequently, even where severe vibration is exerted, the lower end of the housing member 12 can be prevented from being exposed to air, so that in-flow of air into the housing member 12 can be prevented or obviated.

Figure 4A:
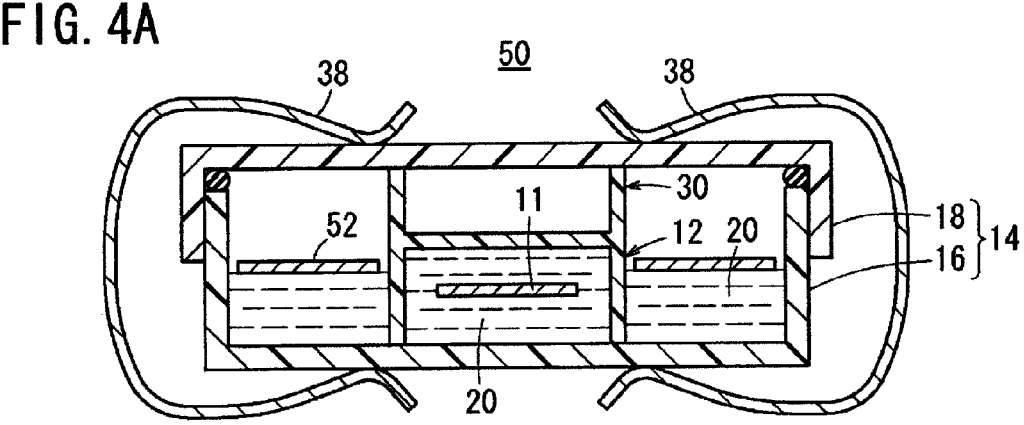
FIG. 4A is a sectional view of a container assembly for containing a biological graft according to a modification of the embodiment shown in FIG. 1.
Figure 4B:
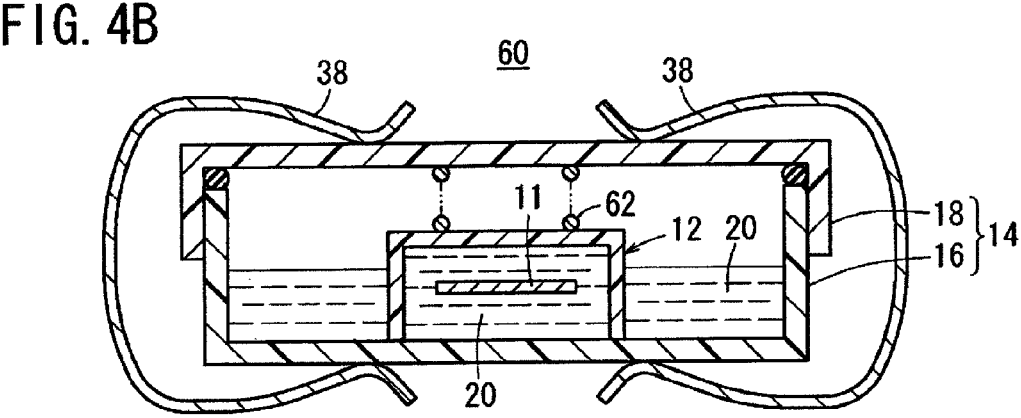
FIG. 4B is a sectional view of a container assembly for containing a biological graft according to another modification of the embodiment of FIG. 1.

Instead of providing the specific intervening member 30 shown in FIG. 1, an intervening member in the form of an elastic member 62 may be disposed between the housing member 12 and the covering member 18, as in the container 60 according to a modification shown in FIG. 4B. While the elastic member 62 is a compression spring in the form of a coil spring in the example shown in the figure, it may be a sponge member or a rubber-made spring. In addition, the elastic member 62 may be anchored to an upper portion of the housing member 12 or the lower surface of the covering member 18, or may be a member independent (separable) from the housing member 12 and the covering member 18.

Figure 4C:
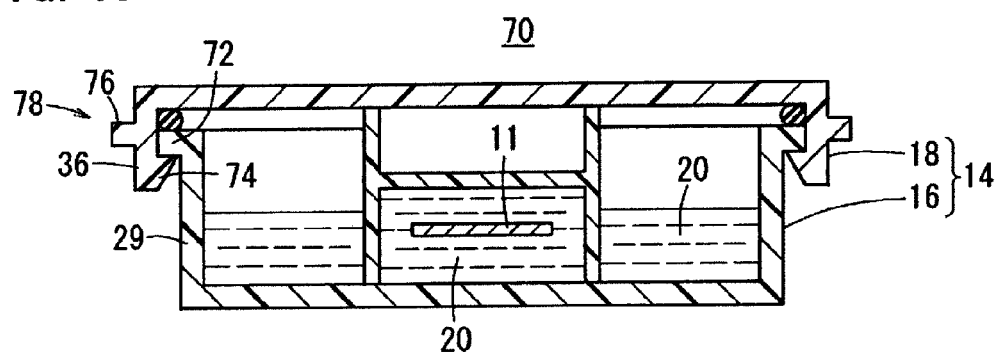
FIG. 4C is a sectional view of a container assembly for containing a biological graft according to another modification of the embodiment of FIG. 1.

Instead of providing the connecting mechanism 22 in the form of the clips 38 as described above, a configuration as in a container 70 according to another modification shown in FIG. 4C may be adopted. In this configuration, a flange section 72 can be provided which projects to the outside (radially outward) from the upper end of the side wall section 29 of the container body 16, and a claw section 74 engageable with the flange section 72 can be provided along the inner circumference of the lower end of the side wall section 36 of the covering member 18. In this embodiment, in order to dismount the covering member 18 from the container body 16, the claw section 74 is spread (elastically deformed) to the outside, to disengage the claw section 74 and the flange section 72 from each other. In this case, a projection 76 projecting outward may be provided on the outside of the side wall section 36 of the covering member 18. This ensures that, by putting fingers on the projection 76 and pulling the projection 76 upward, it is possible to displace the claw section 74 to the outside and, hence, to easily dismount the covering member 18.

Thus, in the container 70, the connecting mechanism 78 including the flange section 72 and the claw section 74 can be adopted. This makes it possible to reduce the number of component parts, and to connect the covering member 18 and the container body 16 to each other more easily.

Now, referring to FIG. 5, a container assembly 80 for containing a biological graft (hereafter referred to simply as "container 80") according to another embodiment of the present technology will be described below. The container 80 is a device to be used for storage and/or transportation of a biological graft 11 having cells that are derived from a biological body. The container 80 can include a housing member 82 for containing the biological graft 11, an outer housing member 88 which includes a container body (outer housing member body) 84 and a covering member 86 and contains the housing member 82. The container can include a storage solution (aqueous fluid) 20 contained in the housing member 82 and the outer housing member 88. The container 80 can also include a connecting mechanism 90 for connecting the container body 84 of the outer housing member 88 and the covering member 86 to each other. Now, the configuration of the container 80 will be described below, the description being made to center on differences of the presently described embodiment from the embodiment shown in FIG. 1.

The housing member 82 differs from the housing member 12, in that the housing member 82 is formed with a hole (through-hole) 94 in an upper wall 92 thereof and the hole 94 is closed with an occluding member 96. In the example shown, the occluding member 96 is a frustoconical plug member formed from a rubber material, for example. In place of the configuration including the hole 94 and the occluding member 96 in the example shown, a configuration may be adopted in which a hollow cylindrical projection projecting upward is provided on the upper side of the hole 94, and an occluding member 96 in the form of a hollow cylindrical cap opening to the lower side and closed at an upper portion is mounted to the projection, thereby effecting occlusion.

The housing member 82 can be filled up with the storage solution 20, without leaving air or bubbles therein, and the biological graft 11 can be contained in a suspended state in the storage solution 20.

The container body 84 of the outer housing member 88 differs from the container body 16 in the embodiment of FIG. 1, in that its bottom section 98 is provided with a horizontal positioning-determining member 100 and that its side wall section 102 is formed with a male screw 104. The horizontal positioning-determining member 100 has a function of horizontally positioning the housing member 82 relative to the container body 84 by engaging with the lower end of the housing member 82. The horizontal positioning-determining member 100 in the example shown in the figure is a circular groove having an inside diameter slightly greater than the outside diameter of the lower end of the housing member 82. The configuration of the horizontal positioning-determining member 100 is not restricted to the above-described structure; instead, the horizontal positioning-determining member 100 may be an annular groove, or may be projections projecting upward at a plurality of positions arranged along the circumferential direction. The male screw 104 can be formed at an outer peripheral part of an upper portion of the side wall section 102.

The covering member 86 of the outer housing member 88 differs from the covering member 18 of the embodiment of FIG. 1 in that its side wall section 106 is provided at the inner periphery thereof with a female screw 108 capable of engagement with the male screw 104. When the female screw 108 of the covering member 86 is engaged with the male screw 104 of the container body 84, the covering member 88 and the container body 84 are securely connected to each other, and the outer housing member 88 is hermetically sealed with a seal member 37 clamped between the covering member 86 and the container body 84. Thus, in the present embodiment, the connecting mechanism 90 is composed of the male screw 104 formed on the container body 84 and the female screw 108 formed on the covering member 86.

Figure 6A:
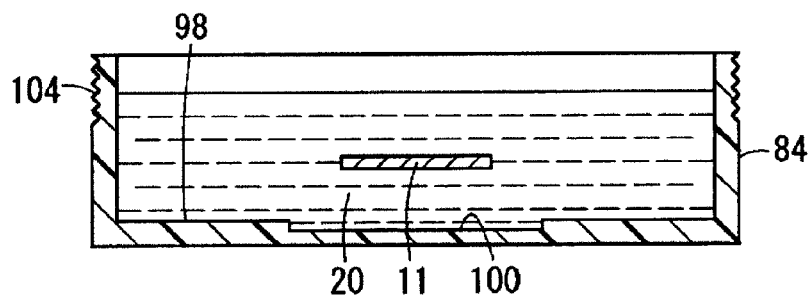
FIG. 6A is a view of a first state illustrating a method of assembling the container assembly shown in FIG. 5.

In one example of how to assemble the container 80 as described above, first, as shown in FIG. 6A, the storage solution 20 can be placed in the container body 84, and the biological graft 11 can be suspended in the storage solution 20.

Figure 6B:
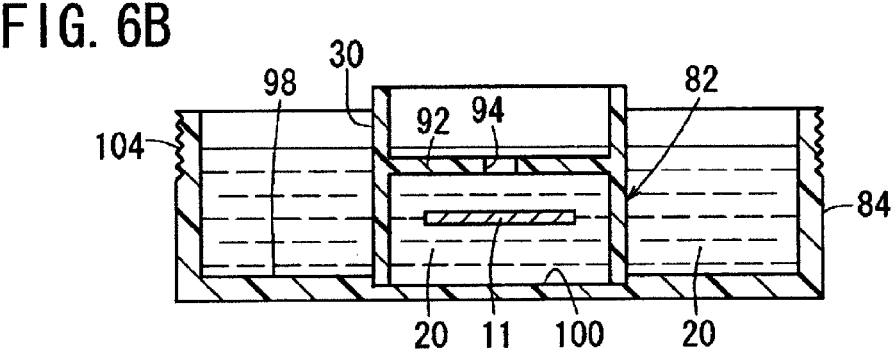
FIG. 6B is a view of a second state illustrating the method of assembling the container assembly shown in FIG. 5.

Next, as shown in FIG. 6B, the housing member 82 can be placed on the surface of a bottom section 98 of the container body 84 in such a manner that the biological graft 11 and the surrounding storage solution 20 are covered with the housing member 82. Incidentally, the storage solution 20 can be preliminarily placed at the stage of FIG. 6A in such a manner that, when the housing member 82 is placed on the surface of the bottom section 98 of the container body 84, the liquid level of the storage solution 20 is above the upper wall 92 of the housing member 82.

During the process of gradually sinking the housing member 82 into the storage solution 20 contained in the container body 84, it is ensured, due to the presence of the hole 94 provided in the upper wall 92 of the housing member 82, that air inside the housing member 82 is discharged through the hole 94, resulting in that the housing body 82 is filled up with the storage solution 20. Since the air inside the housing member 82 can be discharged through the hole 94, the inside of the housing member 82 can be filled up with the storage solution 20 easily and speedily. If necessary, the air inside the housing member 82 can be discharged by use of suction means having a tubular member.

Figure 6C:
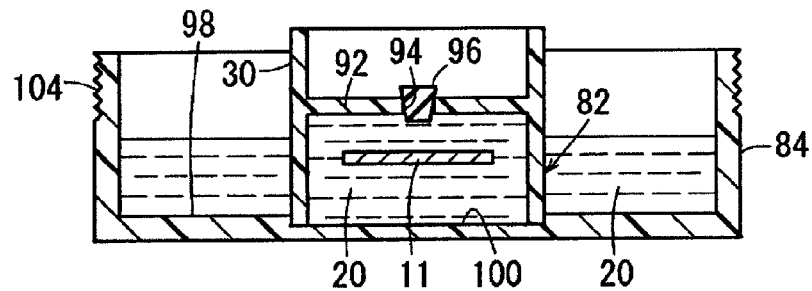
FIG. 6C is a view of a third state illustrating the method of assembling the container assembly shown in FIG. 5.

Subsequently, as shown in FIG. 6C, the hole 94 is closed with the occluding member 96, and the amount of the storage solution 20 present outside the housing member 82 in the inside of the container body 84 can be adjusted to lower the liquid level there, in such a manner that the liquid level of the storage solution 20 outside the housing member 82 in the inside of the container body 84 will be below the liquid level of the storage solution 20 inside the housing member 82. The storage solution 20 having entered the intervening member 30 is removed, as desired.

Figure 6D:
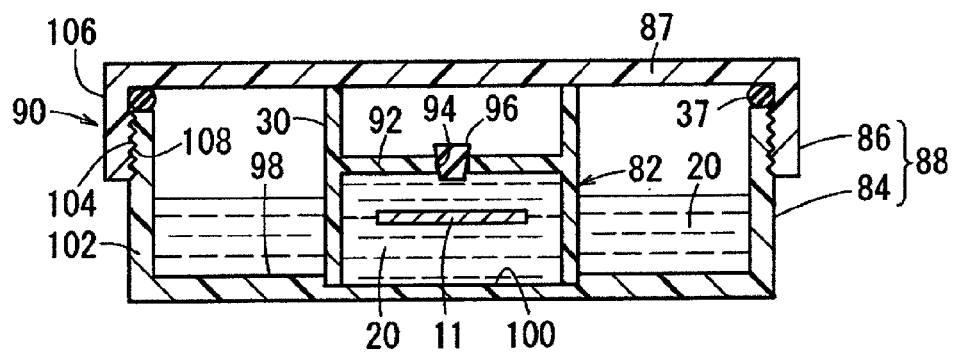
FIG. 6D is a view of a fourth state illustrating the method of assembling the container assembly shown in FIG. 5.

Then, as shown in FIG. 6D, the covering member 86 can be put into screw engagement with the container body 84, whereby the container body 84 and the covering member 86 are connected to each other. Since the container body 84 and the covering member 86 are connected to each other by the screw engagement structure, it is ensured in the connecting mechanism 90 in the present embodiment that the number of component parts can be reduced, as compared with the above-described case of fixation by the clips 38, and that the container body 84 and the covering member 86 can be connected easily and quickly.

After the container body 84 and the covering member 86 are connected to each other, the housing member 82 is clamped between the covering member 86 and the container body 84 through the intervening member 30, so that the housing member 82 is stably fixed inside the outer housing member 88. In addition, the horizontal positioning-determining member 100 prevents the housing member 82 from being horizontally shifted in relation to the container body 84, whereby the biological graft 11 can be held stably.

Figure 5:
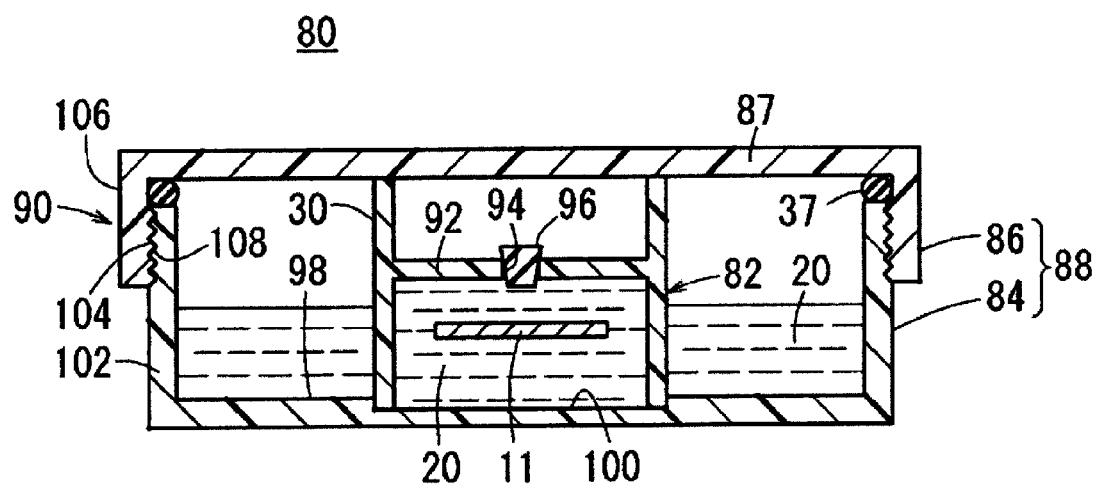
FIG. 5 is a sectional view of a container assembly for containing a biological graft according to another embodiment of the presently disclosed subject matter.

By the above-mentioned process, the container 80 in the state shown in FIG. 5 can be completed. Incidentally, the working steps of assembling the container 80 can be carried out in a clean room (in an aseptic environment).

In order to take out the biological graft 11 from the container 80 in the state shown in FIG. 5, the covering member 86 and the container body 84 can be rotated relative to each other to release the screw engagement therebetween, whereby the covering member 86 is dismounted from the container body 84. Next, the occluding member 96 is removed from the hole 94, and then the housing member 82 is gradually lifted up in relation to the container body 84. Attendant on the upward movement of the housing member 82, air flows through the hole 94 into the housing member 82, so that the storage solution 20 and the biological graft 11 having been contained in the housing member 82 are left in the container body 84. After the biological graft 11 is suspended in the storage solution 20 inside the container body 84, the biological graft 11 can be taken out from the storage solution 20 by an appropriate instrument (a transplanting device or the like), to be served for curing treatment such as transplantation to a patient.

Incidentally, in the embodiment of FIG. 5, with respect to components in common with the first embodiment above, operations and effects which are the same as or similar to those offered by the common components of the first embodiment can be obtained, naturally.

In the container 80 shown in FIG. 5, the stabilizing member 52 shown in FIG. 4A may further be provided. Part of the container 80 may also be replaced by configurations shown in the embodiment of FIG. 1; for instance, the intervening member 30 in the container 80 may be replaced by the elastic member 62 shown in FIG. 4B. In addition, the connecting mechanism 90 in the container 80 may be replaced by the connecting mechanism 22 including the clips 38 (see FIG. 1) or by the connecting mechanism 78 including the claw section 74 and the flange section 72 (see FIG. 4C).

Figure 7:
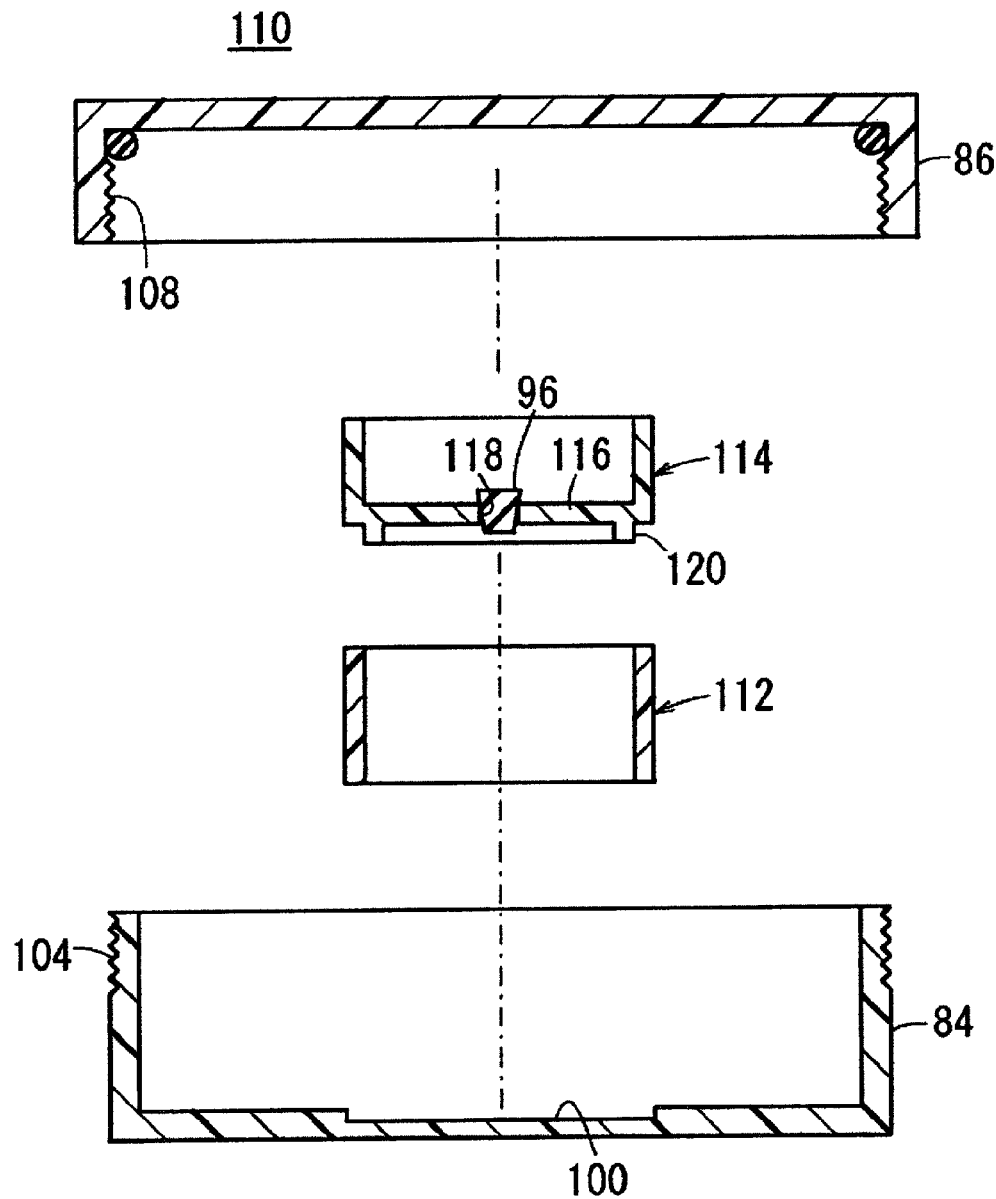
FIG. 7 is an exploded perspective view of a container assembly for containing a biological graft according to a modification of the embodiment of FIG. 5.

In the container 80 shown in FIG. 5, the above-mentioned housing member 82 and intervening member 30 may be replaced, respectively, by a housing member 112 composed of a tubular body with an opening on the upper and lower sides, and by an intervening member 114 configured to close an upper portion of the housing member 112, as shown in FIG. 7 in which a container 110 according to a modification of the embodiment shown in FIG. 5 is depicted. Specifically, the housing member 112 and the intervening member 114 can be configured independently (as separate component parts). A bottom section 116 of the intervening member 114 is a substitute for the upper wall 92 of the housing member 82 shown in FIG. 5, and is formed therein with a hole 118, which is closed by fitting an occluding member 96 therein. The intervening member 114 can include a positioning projection 120 projecting downward from a lower surface of the intervening member 114.

Figure 8A:
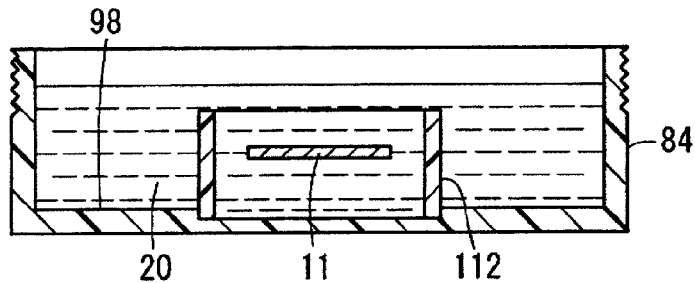
FIG. 8A is a view of a first state illustrating a method of assembling the container assembly shown in FIG. 7.

In order to assemble the container 110 as described above, first, like in FIG. 6A, the storage solution 20 can be placed in the container body 84, and the biological graft 11 can be suspended in the storage solution 20. Next, as shown in FIG. 8A, the housing member 112 can be mounted on the surface of a bottom section 98 of the container body 84 in such a manner as to surround the biological graft 11. Incidentally, at the stage of FIG. 6A, the amount of the storage solution 20 to be placed can be preliminarily adjusted in such a manner that the surface of the storage solution 20 is above the upper end of the housing member 112 when the housing member 112 is mounted on the surface of the bottom section 98 of the container body 84.

Figure 8B:
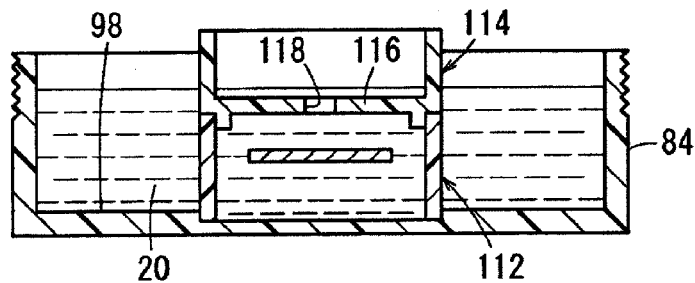
FIG. 8B is a view of a second state illustrating the method of assembling the container assembly shown in FIG. 7.
Figure 8C:
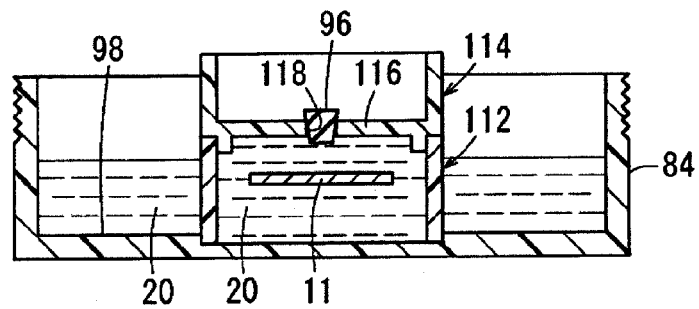
FIG. 8C is a view of a third state illustrating the method of assembling the container assembly shown in FIG. 7.

Subsequently, as shown in FIG. 8B, the intervening member 114 can be mounted on the housing member 112. During the process of gradually sinking the intervening member 114 into the storage solution 20, it is ensured, due to the presence of the hole 118 formed in the bottom section 116 of the intervening member 114, that the storage solution 20 flows through the hole 118 into the intervening member 114.

Next, the hole 118 is closed with the occluding member 96, and the amount of the storage solution 20 present outside the housing member 112 in the inside of the container body 84 can be adjusted to lower the liquid surface so that the liquid surface of the storage solution 20 outside the housing member 112 in the inside of the container body 84 will be below the liquid surface of the storage solution 20 inside the housing member 112. The storage solution 20 having entered the intervening member 114 can be removed, as desired.

Figure 8D:
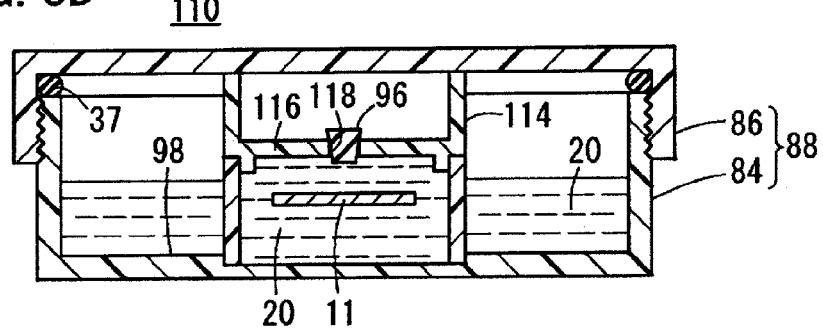
FIG. 8D is a view of a fourth state illustrating the method of assembling the container assembly shown in FIG. 7.

Then, as shown in FIG. 8D, the covering member 86 can be put into screw engagement with the container body 84, whereby the container body 84 and the covering member 86 are connected to each other. After the container body 84 and the covering member 86 are connected to each other, the housing member 112 is clamped between the covering member 86 and the container body 84 through the intervening member 114, so that the housing member 112 is stably fixed inside the outer housing member 88. By the above-mentioned process, the container 110 can be completed.

In the container 80 shown in FIG. 5, the above-mentioned housing member 82 and intervening member 30 may be replaced by a configuration shown in FIG. 9. Specifically, a container 130 according to a modification of the embodiment shown in FIG. 5 can be provided in which a housing member 132 and an intervening member 134 are separate from each other, and the intervening member 134 is formed integrally with the lower surface of a top section 87 of a covering member 86. The housing member 132 can include an upper surface provided with a positioning projection 136 projecting upward.

Figure 10A:
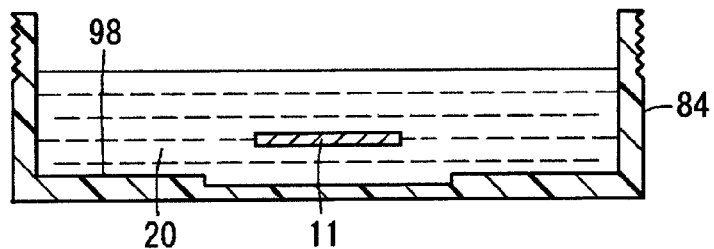
FIG. 10A is a view of a first state illustrating a method of assembling the container assembly shown in FIG. 9.
Figure 10B:
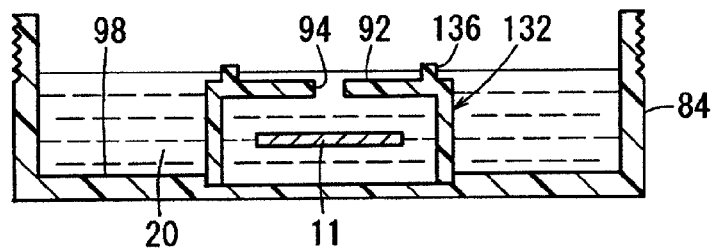
FIG. 10B is a view of a second state illustrating the method of assembling the container assembly shown in FIG. 9.

In order to assemble the container 130 configured as described above, first, as shown in FIG. 10A, the storage solution 20 can be placed in the container body 84, and the biological graft 11 can be suspended in the storage solution 20. Next, as shown in FIG. 10B, the housing member 132 can be mounted on the surface of a bottom section 98 of the container body 84 in such a manner as to surround the biological graft 11. Incidentally, at the stage of FIG. 10A, the amount of the storage solution 20 to be placed can be adjusted such that the liquid surface of the storage solution 20 is above an upper wall 92 of the housing member 132 when the housing member 132 is mounted on the surface of the bottom section 98 of the container body 84.

During the process of sinking the housing member 132 into the storage solution 20 in the container body, it is ensured, due to the presence of the hole 94 formed in the upper wall 92 of the housing member 132, that air present inside the housing member 132 is discharged through the hole 94, so that the housing member 132 is filled up with the storage solution 20. Since the air inside the housing member 132 can thus be discharged through the hole 94, the inside of the housing member 132 can be filled up with the storage solution 20 easily and speedily.

Figure 10C:
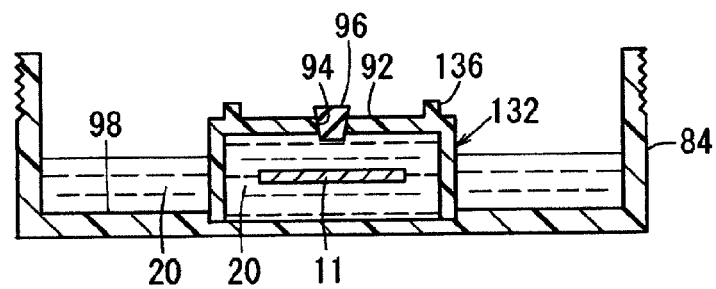
FIG. 10C is a view of a third state illustrating the method of assembling the container assembly shown in FIG. 9; and, FIG. 10D is a view of a fourth state illustrating the method of assembling the container assembly shown in FIG. 9.

Subsequently, as shown in FIG. 10C, the hole 94 can be closed with an occluding member 96, and the amount of the storage solution 20 present outside the housing member 132 in the inside of the container body 84 can be adjusted to lower the liquid surface there, in such a manner that the liquid level of the storage solution 20 outside the housing member 132 in the inside of the container body 84 is below the liquid level of the storage solution 20 inside the housing member 132.

Figure 10D:
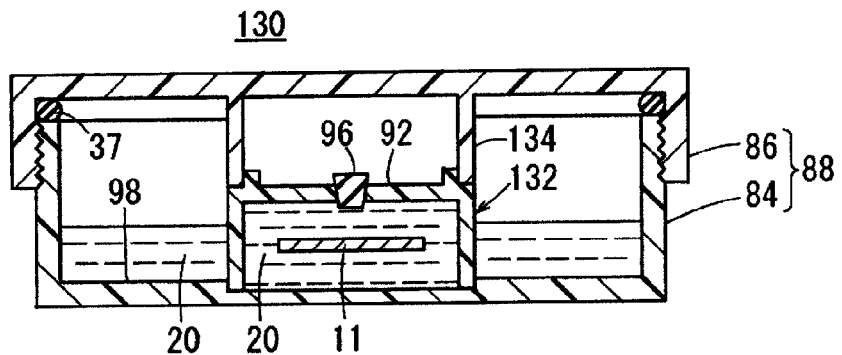

Then, as shown in FIG. 10D, the covering member 86 can be put into screw engagement with the container body 84, whereby the container body 84 and the covering member 86 are connected to each other. Since the intervening member 134 is integrated with the covering member 86, the housing member 132 is pressed against the surface of the bottom section 98 of the container body 84 by the intervening member 134, so that the housing member 132 is stably fixed inside the outer housing member 88. By the above-mentioned process, the container 130 can be completed.

It should be noted that any of the different structures and method steps disclosed in each of the above specific embodiments can be used interchangeably with other and similar different structures and methods steps of the other disclosed embodiments.

While the presently disclosed subject matter has been described by showing some exemplary embodiments above, the disclosed subject matter is not to be limited to the above embodiments, and various modifications can naturally be made within the scope of the gist of the invention.

What is claimed is:

1. A container assembly for containing a biological graft, comprising:
   an outer housing member
   a non-porous housing member adjustably positioned inside the outer housing member and sized to be able to contain the biological graft while keeping the size of an original shape of the biological graft; and
   an aqueous fluid filling a space bounded by the housing member and at least one surface of the outer housing member,
   wherein the housing member and aqueous fluid are configured such that the biological graft is contained in a suspended state in the aqueous fluid,
   and substantially no air is contained in the space.

2. The container assembly according to claim 1, further comprising:
   an outer housing member configured to contain the housing member,
   wherein the housing member has a lower-side opening section which is open to a lower side and is greater in plan-view shape than the biological graft, and
   the lower-side opening section is closed by contact of a lower circumferential end of the housing member with a surface of a bottom section of the outer housing member.

3. The container assembly according to claim 2, wherein a fluid which is the same as or different from the aqueous fluid is contained in the outer housing member outside of the housing member.

4. The container assembly according to claim 3, further comprising:
   a stabilizing member floating on the surface of the fluid present outside the housing member and in the outer housing member.

5. The container assembly according to claim 2, wherein a gel-like material is contained in the outer housing member outside of the housing member.

6. The container assembly according to claim 2, wherein the outer housing member has an outer housing member body having an upper-side opening section open to the upper side and a covering member configured to close the upper-side opening section,
   the container assembly further includes
     a connecting mechanism configured to connect the outer housing member body and the covering member to each other, and
     an intervening member configured to be clamped between the lower-side opening section of the housing member and the covering member when the outer housing member body is closed with the covering member.

7. The container assembly according to claim 6, wherein an upper end of the intervening member forms line or surface contact with the covering member when the outer housing member body is closed with the covering member.

8. The container assembly according to claim 6, wherein the connecting mechanism includes at least one clip configured to make contact with a lower surface of the outer housing member body and an upper surface of the covering member to thereby constrain the outer housing member body and the covering member.

9. The container assembly according to claim 2, wherein a wall of the housing member includes a hole in communication with an area inside of the housing member and an area outside of the housing member, the housing member includes an occluding member, and the hole is configured to be closed with the occluding member.

10. The container assembly according to claim 2, wherein the outer housing member body includes a horizontal positioning-determining member configured to horizontally position the housing member relative to the outer housing member body, wherein the horizontal positioning-determining member is located at a bottom section of the outer housing member body.

11. A container assembly configured to contain a biological graft, comprising:
a housing member having a top end, a lower end, and a wall located at the lower end defining a lower end opening in the housing member;
a container body including a lower surface configured to mate with the wall of the lower end opening of the housing member to define a non-porous chamber within the housing member, the chamber being configured to contain aqueous fluid and the biological graft suspended in the aqueous fluid such that the aqueous fluid cannot escape from the non-porous chamber during use;
a covering member configured to connect to the container body and contact with the housing member to maintain contact between the wall of the lower end opening of the housing member and the lower surface of the container body in order to form the chamber; and
a connecting structure configured to connect the covering member and the container body and to maintain contact between the wall of the lower end opening of the housing member and the lower surface of the container body in order to form the chamber.

12. The container assembly according to claim 11, wherein the connecting structure is one of, a clip, and a screw and thread structure located on the container body and the covering member.

13. The container assembly according to claim 11, wherein the housing member includes an aperture in the top end and an occluding member configured to seal the aperture in the housing member such that the chamber is hermetically sealed when the occluding member is located in the aperture and the container body is connected with the covering member by the connecting structure.

14. The container assembly according to claim 11, wherein the housing member includes an intervening member located at the top end of the housing member and configured to contact the covering member and be clamped between the covering member and the container body when the container body is closed with the covering member.

* * * * *